United States Patent [19]

Patch

[11] Patent Number: 4,504,230
[45] Date of Patent: Mar. 12, 1985

[54] PREFABRICATED DENTAL ONLAYS AND METHOD THEREFOR

[75] Inventor: Stanley J. Patch, Great Lakes, Ill.

[73] Assignee: The United States of America as represented by the Secretary of the Navy, Washington, D.C.

[21] Appl. No.: 478,577

[22] Filed: Mar. 23, 1983

[51] Int. Cl.³ .............................................. A61C 5/08
[52] U.S. Cl. .................................................. 433/219
[58] Field of Search ................................ 433/218, 219

[56] References Cited

U.S. PATENT DOCUMENTS

| 996,921 | 7/1911 | Goslee | 433/218 |
| 3,328,879 | 7/1967 | Bax | 433/218 |
| 3,797,114 | 3/1974 | Wiland | 433/219 |

Primary Examiner—Robert Peshock
Attorney, Agent, or Firm—Robert F. Beers; Frederick A. Wein

[57] ABSTRACT

Prefabricated dental crowns which do not require precision fitting are presented. In one embodiment, the crown is secured to a preparatory foundation disposed upon a tooth. In a second embodiment, a ring-like crown body is secured to the tooth by a filler material and a crown overlay having an occlusal portion is matingly fitted and secured to the crown body.

5 Claims, 4 Drawing Figures

4,504,230

PREFABRICATED DENTAL ONLAYS AND METHOD THEREFOR

BACKGROUND

The present invention relates to dental prosthetic devices, and more particularly, to crowns.

The prior art methods for providing crowns on teeth are very labor intensive and expensive. Such procedures require the making of molds from the patient's mouth and casting a precisely fitting crown from such molds. This is called the "indirect technique" because the work is accomplished at a laboratory distant from the patient.

Another procedure for providing crowns is to use prefabricated crowns, often made of a non-corrosive material such as stainless steel. These prefabricated crowns often cannot be used for restorations because of the great difficulty of achieving an adequate fit and adequate relationship to the adjacent and opposing teeth. Additionally, the prefabricated crowns are often thin walled and unable to withstand the forces exerted during biting or chewing without wear. Additionally, these prefabricated crowns have almost no adjustment capability and cannot be shaped by a dental bit due to the thin wall.

In addition to the cost and complexity of the indirect technique and the difficult problem of fitting a prefabricated crown, the prefabricated crowns have the problem that if the crown is ever damaged or falls off, the underlying tooth is left exposed. The pain caused by this exposure can result in a disabling emergency situation.

Additionally, teeth prepared for indirect fabrication crowns require extensive removal of external tooth structure usually extending beneath the gingival crest. This results in tooth sensitivity and gingival injury with a danger of development of periodontal disease.

Accordingly, it is desirable to provide dental crowns and methods therefor which are inexpensive and can be fitted right in the patient's mouth without subsequent molds being required. It is also desirable to provide dental crowns and methods therefor which can be prefabricated and do not require precision fitted prefabricated devices. It is also desirable to provide a dental crown which when damaged or lost, the tooth will still be protected. It is further desirable to provide a prefabricated crown which is adjustable at the time of installation.

SUMMARY OF THE INVENTION

Briefly, the present invention relates to dental crowns which do not require precision fitting. In one embodiment, a crown having wall thickness sufficient to withstand occlusal pressure is secured upon a preparatory foundation disposed upon a tooth. In a second embodiment, a ring-like crown body is secured to the tooth by a filler material and a crown overlay having the occlusal portion is matingly fitted and secured to the crown body.

Accordingly, it is an object of the present invention to provide dental crowns and methods therefor which can be fitted directly in the patient's mouth. It is another object of the present invention to provide dental crowns and methods therefor which can be prefabricated and do not require a precision fit of the tooth for installation. A further object of the present invention is to provide dental crowns which if damaged or lost, provide means for continued protection of the tooth. Still another object of the present invention is to provide a dental crown which can be installed upon a preparatory foundation disposed on the tooth. Yet another object of the present invention is to provide a dental crown overlay installed upon a crown body which is filled with a supporting filler material and secured to the tooth.

Further objects and advantages of the present invention will become apparent as the following description proceeds and features of novelty characterizing the invention will be pointed out with particularity in the claims annexed to and forming a part of this specification.

DESCRIPTION OF THE DRAWINGS

For a better understanding of the present invention reference may be had to the accompanying drawings wherein.

DETAILED DESCRIPTION OF THE PREFERRED EMBODIMENT

Figure 1:
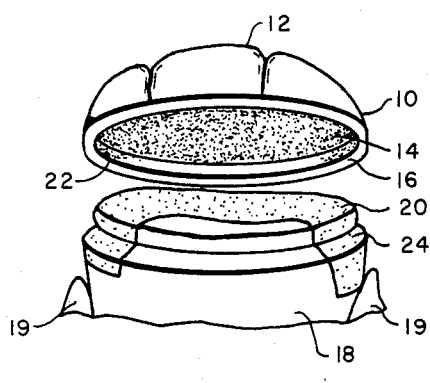
FIG. 1 is an exploded isometric view of a first embodiment of the present invention showing a crown securable to a tooth having a preparatory foundation.

Referring now to the drawings wherein like reference numerals have been applied to like members, FIG. 1 shows a first embodiment of the present invention. As discussed above, the indirect method for providing crowns is very cumbersome and costly, requiring precision molds be taken of the teeth and a precision fitting crown be produced by the lost-wax method with the end product being the crown. Each mold produced introduces inaccuracies which will effect the fit of the resulting crown. The necessity of the crown to fit precisely requires that great care be taken and that the procedure be very labor intensive and require great skill. Additionally, there is a substantial time delay inasmuch as the crown is produced at a distant laboratory.

Referring now to FIG. 1 there is shown a crown 10, having an occlusal surface 12, an internal securement surface 14, and a peripheral rim 16. Crown 10 is mountable onto a tooth 18 held by gingiva 19 and upon which is disposed a preparatory foundation 20.

More specifically, the crown 10 can be installed on badly broken teeth, in which case the preparatory foundation 20 can be extensive. The foundation 20 is a shaped amalgam which is condensed onto tooth 18 to build up the tooth for providing a proper foundation for crown 10. Additionally, should anything adverse happen to crown 10 such as damage or total loss, the tooth will remain protected by a dental composite resin discussed hereinafter used to glue the crown 10 to tooth 18.

The crown 10 is designed to withstand biting pressure at the occlusal surface 12 without being in direct contact with the tooth 18. Thus, crown 10 is provided with a wall thickness which is greater than the wall thickness of a typical prefabricated crown, i.e. at least one millimeter thick, which additionally provides sufficient wall thickness to permit trimming adjustment.

Typically the crown is made of stainless steel but it can also be made of any other appropriate metal or material such as ceramic or porcelain, and depending upon the material, can be produced by stamping, injection molding, or the like.

When installed, crown 10 is mechanically retained to tooth 18. This mechanical retention can be improved by addition of an internal extending ridge 22 being provided about the inner peripheral rim 16 and by undercut ridge 24 on tooth 18. Both ridge 22 and ridge 24 provide additional surface area to mechanically secure crown 10 to tooth 18 by the composite resin material. Alternatively, securement surface 14 can be provided with a roughened surface of microscopic fingers such as produced by an electrolytic or acid etch as appropriate for the material of crown 10, or if crown 10 is produced by injection molding, the roughened surface can be molded directly into surface 14. In such a case sufficient adhesion may be achieved without ridge 22 or ridge 24 which can be eliminated. The securement is provided by a commercially available dental composite resin of the type used for acrylic restoration of teeth in visible areas. These acrylic resins typically have glass quartz and other substances included for abrasion resistance, reduced thermal expansion, and increased hardness. It should be noted that undercut 24 is but one example of a technique used for securing the composite to tooth 18 and the composite resin is also secured to any remaining enamel on the tooth 18 after the enamel has preferrably been prepared with an acid etch.

Crown 10 is installed as follows: Areas of tooth 18 which require subgingival preparation are prepared to receive the amalgam following standard procedures of resistance and retention common to amalgam restorations. In the exemplary embodiment, supra-gingival tooth structure which is well supported is prepared to a shoulder bevel without regard to parallelism with the undercut shoulder 24, if needed. There is no need to create parallel walls or subgingival margins.

Figure 2:
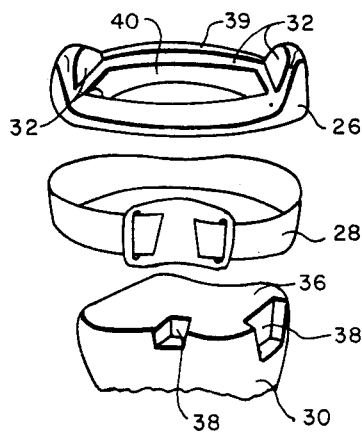
FIG. 2 is an exploded isometric view of a second embodiment of the present invention showing a crown body installable on a tooth.

A matrix band 28 is then installed as similarly shown in FIG. 2 according to standard procedures. The matrix band 28 should seal the entire margin and allow for adjustment after placement but not interfere with occlusion. After placement of matrix 28, the interproximal areas are wedged according to standard procedures. Even the concave interproximal areas can be wedged so that the matrix 28 will closely adapt to the prepared tooth precisely at the finish line.

Amalgam is then condensed into the prepared areas which extend subgingivally until the amalgam is within three millimeters of the occlusal plane. With the matrix 28 in place, the amalgam is carved or cut to accomodate the crown preparation exemplarily shown in FIG. 1. Enamel margins are etched and the entire preparation is washed and dried within the matrix. A proper prefabricated crown 10 is then selected, adjusted proximally, filled with composite resin, and occluded into place within the matrix 28. The crown 10 is held in place by the patient closing his mouth with the matrix assuring that the crown 10 is positioned in proper relationship with adjacent teeth until the resin hardens.

Prior art procedures for prior art stainless steel prefabricted crowns provide poor marginal integrity and limited adjustability. In the present procedure, no attempt is made to achieve contact between the crown margin and the preparation margin. This vertical distance allows the crown to be freely positioned as needed for adequate occlusion and for proper proximal contacts.

The wedges and matrix are then removed and the 1-3 millimeter composite margin between the tooth and crown 10 is trimmed and smoothed. As shown, the area of the composite typically will be supragingival and below the height of the contour and thus will be reasonably protected from crevicular fluids and occlusal abrasion. Because the crowns are provided with a short occluso-cervical dimension, typically about five millimeters, crowns 10 would not require adjustment of the cervical margin.

Additionally, it should be noted that the composite resin intermediary secures the remaining enamel tooth structure for resisting fracture of the tooth. Thus, in the event that damage or loss of the crown 10 should occur, the tooth will still be protected.

Figure 3:
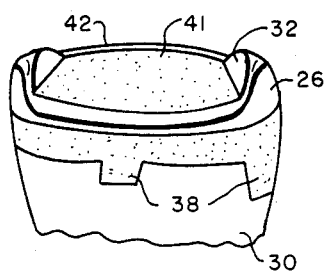
FIG. 3 shows a crown body of FIG. 2 with a filler material installed upon a tooth.
Figure 4:
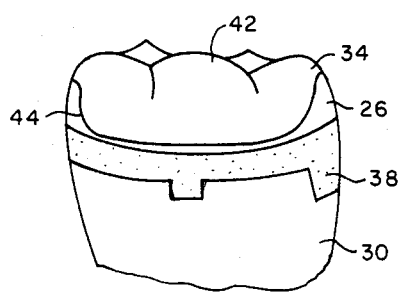
FIG. 4 shows the crown overlay installed upon the crown body of FIG. 3.

Referring now to FIGS. 2-4, therein is shown a second embodiment of the dental crown of the present invention. Shown in FIG. 2 is a crown body 26, a matrix band 28, and a tooth 30. Matingly fittable onto a receiving portion 32 of crown body 26 is a crown overlay 34 (FIG. 4). The occlusal overlay 34 fits snugly within receiving portion 32 except at the proximal surfaces. A receiving surface 36 is prepared on tooth 30 and attachment grooves 38 are provided. The grooves 38 shown are only representative and they can be any shaped depression made in the tooth 30 for securement of amalgam to the tooth using common procedures. After the tooth is prepared, a matrix band 28 is placed on tooth 30 in a manner well known in the art and matrix band 28 can then be wedged. A correct prefabricated crown body 26 is then selected and adjusted in mesio-distal dimension if necessary.

The crown body 26 is ring-like in shape having a wall 39 defining a cavity 40 for receiving a filler material as will be discussed hereinafter. The crown body 26 can be made of any appropriate material as discussed above for crown 10 and similarly produced in an appropriate manner. Wall 39 is provided with internal retention means such as a rough surface or minute protruding fingers or the like of approximately 0.2 millimeters for retention to the tooth 30 by the amalgam 41.

Crown body 26 is positioned within the matrix band 28 and held in place by band 28 or any other appropriate technique such as a temporary glue. Amalgam is then condensed into cavity 40 onto the prepared surface 36 and against band 28 into the marginal areas. The condensation of amalgam fills the entire crown body 26 and into bores 38 as shown in FIG. 3 thus locking crown body 26 integrally with tooth 30 with grooves 38 providing additional securement. It should be noted that the margins of the crown will be amalgam which is condensed against matrix 28. The wedges and matrix 28 are removed and the amalgam is carved approximately flat with an appropriate tool at the occlusal extent 42 of crown body 26. All amalgam margins are smoothed and burnished if necessary.

As shown in FIG. 3, the mesial and distal contacts are intact. The facial and lingual margins are at the cervical of crown body 26. It is preferred that the cervical margin be about one millimeter below the height of greatest convexity.

Referring now to FIG. 4, overlay 34 is provided with an occlusal surface 42 and a securement portion 44 diametrically disposed to occlusal portion 42 for matingly fitting surfaces 32 and wall 39. In the exemplary embodiment, overlay 34 is solid but it is within the contemplation of the present invention that securement surface 42 be concave. Overlay 34 is glued to body 26 using a dental adhesive commonly available, e.g. a polycarboxylate cement made by S.S. White Corp. under the name DURALON ™. This adhesion is not only to the wall 39 but is also to the carved occlusal extent 42 thus providing overlay 34 with a large area of adhesion. Thus, overlay 34 is thicker than ordinary crowns so that it can withstand occlusal pressure without fracturing since it does not touch tooth 30. Also, if overly 34 is damaged or lost, tooth 30 is still protected by body 36 and amalgam 40. In the present embodiment, crown body 26 has the appropriate convexity for contact with adjacent teeth and overlay 34 does not cover the mesial and distal parts of crown body 26.

It should also be noted that in the exemplary embodiment, securement surface 44 is generally flat over the portion in contact with amalgam 40. However, if securement surface 44 is provided with a concave shape to form a hollow within overlay 34, then, in order to provide additional adhesion, sufficient adhesive should be used to generally fill the hollow when overlay 34 is installed onto body 26.

Thus, there is shown inexpensive prefabricated crowns and methods therefor which can be fitted in the dentist's office and do not require custom fabrication. The crowns do not directly contact the natural tooth, and are adjustable and have sufficient wall thickness to withstand biting pressure and provide long term resistance to wear. Additionally, in the event that the crown is damaged or lost, the tooth will still be protected.

While there has been illustrated and described what is at present considered to be a preferred embodiment of the present invention, it will be appreciated that numerous changes and modifications are likely to occur to those skilled in the art and it is intended in the appended claims to cover all those changes and modifications which fall within the true spirit and scope of the present invention.

What is new and desired to be claimed by Letters Patent is:

1. A dental crown comprising:

a generally ring-shaped crown body having a wall and adapted for securing the body to one of a tooth and a preparatory foundation disposed upon the tooth, the wall defining a cavity, the cavity being fillable with a filler material, and an overlay member having an occlusal portion and a securement portion with an adherentable surface, the securement portion being adapted for mating engagement with the wall of the crown body, the crown body having means for receiving a filler material for securing the crown body to the tooth, the securement portion of the overlay member having means for securing the overlay member to the crown body.

2. The dental crown of claim 1 wherein the securing portion comprises a treated surface on the securement portion for receiving an adhering means.

3. The dental crown of claim 1 wherein the securing portion comprises at least one protrusion disposed at the open end of the crown and extending inwardly towards the preparatory foundation when the crown is mounted onto the tooth.

4. The dental crown of claim 3 wherein the at least one protrusion comprises a ridge extending about the inner perimeter of the open end of the crown.

5. A method for installing a crown on a tooth comprising the steps of:

providing a crown body comprising a generally ring-shaped member securable to a tooth and adapted for receiving a matingly fitting overlay crown member, and adapted for receiving a filler material for securing the crown body to the tooth, providing a crown overlay member adapted for matingly fitting the crown body and being secured to the crown body, installing the crown body onto the tooth, filling the crown body with a filler material, and installing the crown overlay member into mating engagement with the crown body and securing the crown overlay member to the crown body member with adhesive.

* * * * *